United States Patent [19]

Bonnet et al.

[11] Patent Number: 4,686,965
[45] Date of Patent: Aug. 18, 1987

[54] INSTRUMENT FOR ENDOSCOPIC OPERATIONS

[75] Inventors: Ludwig Bonnet; Siegfried Hiltebrandt, both of Knittlingen, Fed. Rep. of Germany

[73] Assignee: Richard Wolf GmbH, Fed. Rep. of Germany

[21] Appl. No.: 824,662

[22] Filed: Jan. 31, 1986

[30] Foreign Application Priority Data

Feb. 8, 1985 [DE] Fed. Rep. of Germany ....... 3504292

[51] Int. Cl.⁴ .............................................. A61B 1/00
[52] U.S. Cl. ........................................................ 128/4
[58] Field of Search ...................................... 128/4–8; 73/151

[56] References Cited

U.S. PATENT DOCUMENTS

| 2,599,662 | 1/1952 | Rosenbaum | 128/6 |
| 2,767,705 | 10/1956 | Moore | 128/4 |
| 3,417,746 | 12/1968 | Moore et al. | 128/6 |
| 3,709,214 | 1/1973 | Robertson | 128/6 |
| 3,831,587 | 8/1974 | Boyd | 128/6 |
| 3,870,036 | 3/1975 | Fiore | 128/6 |
| 3,882,852 | 5/1975 | Sinnreich | 128/4 |
| 4,321,915 | 3/1982 | Leighton et al. | 128/4 |
| 4,421,106 | 12/1983 | Uehara | 128/4 |
| 4,471,766 | 9/1984 | Tetrayama | 128/6 |
| 4,573,452 | 3/1986 | Greenberg | 128/6 |

Primary Examiner—Kyle L. Howell
Assistant Examiner—Max F. Hindenburg
Attorney, Agent, or Firm—Hill, Van Santen, Steadman & Simpson

[57] ABSTRACT

An instrument for endoscopic operations has trocar sleeve and a trocar sleeve insert which can be introduced and axially displaced in the trocar sleeve. In the working position, the trocar sleeve insert protrudes beyond the trocar sleeve in the distal region. The trocar sleeve can be fixed by flexible auxiliary instruments in the region of the organ to be treated. The trocar sleeve insert can be fixed in the organ wall by sealing lips.

9 Claims, 4 Drawing Figures

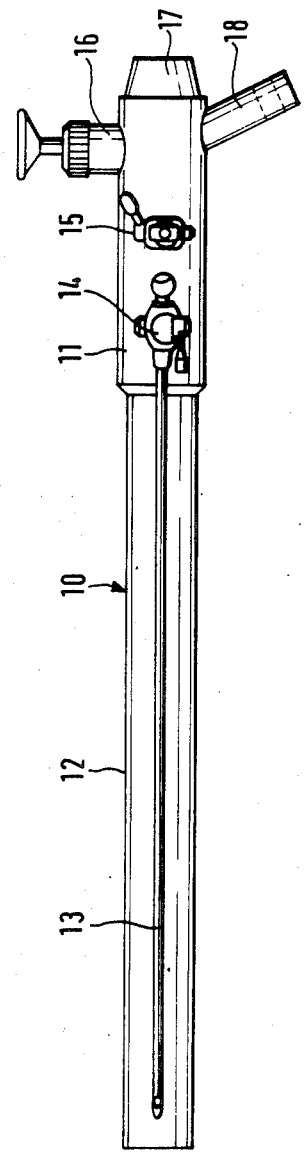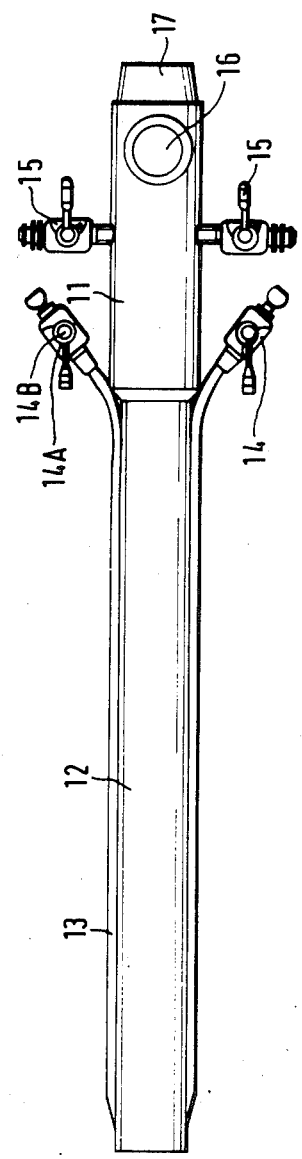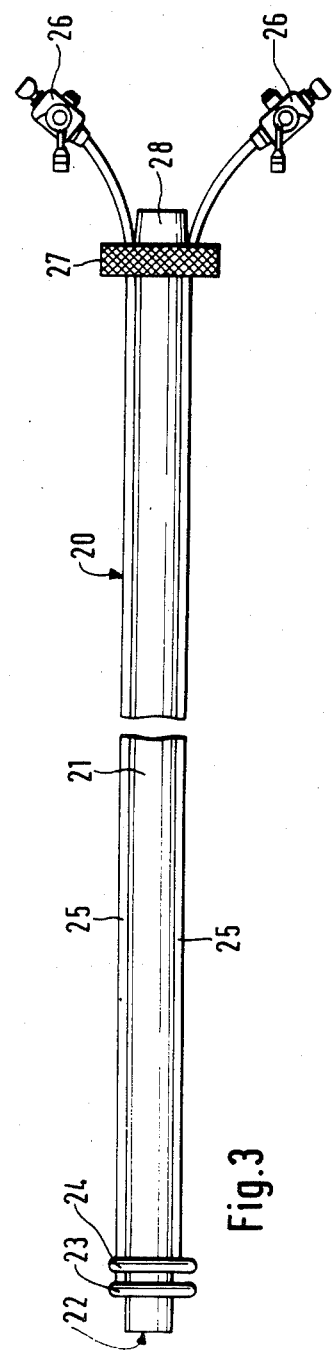

INSTRUMENT FOR ENDOSCOPIC OPERATIONS

This invention relates to an instrument for endoscopic operations, in particular for percutaneous gallstone removal or gall bladder obliteration.

BACKGROUND OF THE INVENTION

Gallstones are usually attributable to an over-concentration of stone-forming substances such as, for example, cholesterol, lime and the like, or else an infection of the gall bladder, and operations for the removal of gallstones are relatively common. Removal of stones accumulated in the gall bladder is, in any case, necessary when they lead to severe colic, which produce cramp-like abdominal pains, outbreaks of sweating, and nausea. At present the removal of gallstones is only possible by open surgery, with all its risks and disadvantages.

DE-OS No. 29 23 105 describes an instrument for gall bladder operations which basically makes endoscopic intervention possible. With this instrument, after the removal of a trocar and a trocar sleeve, a short trocar sleeve insert with relatively wide free operating space is inserted into the abdominal wall and is fixed on the operating table by means of a tripod linkage. Then the operation endoscope or the like is introduced into the body cavity through the trocar sleeve insert.

Although a trocar sleeve insert which is thus fixed may facilitate the endoscopic treatment of organs such as, for example, the gall bladder, it does not ensure that the operation endoscope and the trocar are adequately fixed with respect to the organ to be operated on. A movement or positional change of the patient causes movement of the insert because it is fixed to the operating table. Also there is a risk that the position of the organ to be treated, for example, the gall bladder, may change before or during the operation.

A main object of the present invention is to provide an instrument for endoscopic operations which can be fixed securely in position with respect to the organ to be treated.

SUMMARY

The basic concept of this solution consists in fixing the distal end of the trocar sleeve, which extends close to the organ to be treated, directly on the organ. This is effected by means of flexible or bendable auxiliary instruments which are axially displaceable through instrument channels located on the trocar sleeve outer stem and have at their distal ends grasping forceps which are operable by proximal manipulation. Examples of suitable grasping forceps are described as probes in a nephroscope in DE-GM No. 82 04 847.

With these grasping forceps, the organ to be treated, for example the gall bladder, is grasped, so that axial displacement of the flexible auxiliary instrument relative to the trocar sleeve insert, and thus a positional change of the organ to be treated is prevented by fixing of the proximal ends of the auxiliary instruments on the trocar sleeve insert. Thus, a trocar sleeve insert can be introduced through the trocar sleeve up to a predetermined point of the organ to be treated, and into that organ, and an instrument channel is created leading to the organ to be treated. For fixing the distal end of the trocar sleeve insert on the organ and ensuring a seal between organ wall and trocar sleeve insert, sealing lips, for example of the type described in DE-GM No. 77 36 389, are provided in this region, which sealing lips are in fluid-tight contact with the outer and inner walls of the organ.

The instrument channels may be on the outside of the trocar sleeve stem in a similar way to the guide tubes for flexible instruments in a cystoscope in accordance with DE-OS No. 28 43 151.

BRIEF DESCRIPTION OF THE DRAWINGS

An embodiment of the invention is described in detail below, by way of example, with reference to the accompanying drawings in which:

FIG. 1 is a side view of a trocar sleeve which is part of an instrument according to the invention, FIG. 2 is a plan view of the trocar sleeve of FIG. 1, FIG. 3 illustrates a side view of a trocar sleeve insert for insertion in the trocar sleeve insert of FIGS. 1 and 2.

DETAILED DESCRIPTION

Figure 4:
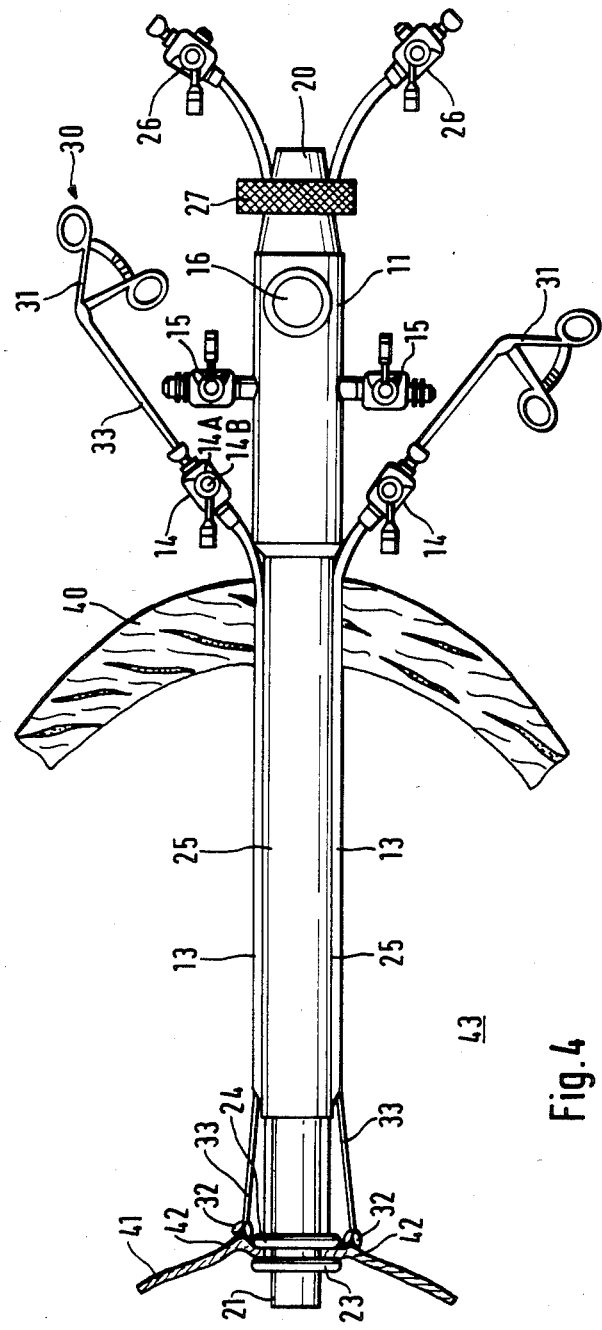
FIG. 4 is a diagrammatic representation of the instrument according to the invention in use in the human abdominal space, with the insert of FIG. 3 in the trocar sleeve of FIGS. 1 and 2.

FIGS. 1 to 3 illustrate in detail two parts of an instrument for endoscopic operations, namely a trocar sleeve 10 and a trocar sleeve insert 20, which are combined to form the instrument according to the invention as illustrated in FIG. 4.

The trocar sleeve 10, as is generally known, includes a base member 11 from which a tubular stem 12 extends. Connection spigots 15, which can be closed, and a valve for the introduction of gas are fixed on the base member 11. The proximal end of the trocar sleeve 10 is closed by a removable sealing cap 17, preferably of rubber, and is formed with a passage, not shown. Novel axially extending instrument channels 13 are fixed on the sides of the tubular stem 12 of the trocar sleeve 10, through which channels flexible auxiliary instruments can be threaded. The channels extend from valved connectors 14 in the region of the base member, and have open distal ends. The instrument channels 13 are mounted on the outside of the tube 12 so that the internal cross-section of the tube 12 can be as large as possible. The internal diameter of the channels 13 is chosen such that all customary flexible instruments, for example grasping forceps or the like, can be introduced into the channels. The flexible or bendable outer stem of such an auxiliary instrument can be fixed by a bush 14B which is rotatable in the housing 14A of a connector spigot 14.

Fixing means are provided near the outer end of the base member 11 of the trocar sleeve 10. The fixing means is shown as a metal pin 18 which has a round, rectangular or quadrilateral cross-section. The trocar sleeve can be detachably fixed on an operating table by known fastening means, not shown.

A trocar sleeve insert 20 which can be pushed into the trocar sleeve of FIGS. 1 and 2, is illustrated in FIG. 3. This trocar sleeve insert 20 has a stem 21 which defines a working channel 22 and has an annular shoulder 27 at its proximal end.

Two inflatable sealing lips 23 and 24 are axially spaced from each other on the distal end of the stem 21, which lips are inflatable via supply lines 25 and the connection valves 26. One design of these sealing lips is described in detail in DE-GM No. 77 36 389.

At its proximal end the trocar sleeve insert 20 can be closed by a coupling element or preferably by a sealing cap 28 having a guide passage. The dimensions of the working channel 22 of the trocar sleeve insert 20 are such that a surgical optical system and/or auxiliary instruments or the like can be introduced into that working channel for endoscopic investigation and surgery.

The design and use of the instrument will now be explained with reference to FIG. 4, which illustrated diagrammatically the percutaneous removal of gallstones.

With the instrument according to the invention, gallstones can be removed or the gall bladder eliminated. For preparation of the operation, the abdominal wall 40 is first punctured by means of a thin insufflation needle through which a gas which is tolerated by the body is introduced into the abdominal space 43 and the abdominal wall 40 is raised from the underlying organs, not shown. A small incision is then made in the abdominal wall 40 at a point suitable for the endoscopic insertion, through which incision the trocar sleeve 10 and the trocar located therein are introduced into the body cavity. The trocar is then removed and the distal end of the trocar sleeve 10 is moved into the vicinity of the organ to be treated, in this case the gall bladder. The wall of the gall bladder 41 is not yet punctured. Firstly a surgical optical system is introduced into the body cavity through the trocar sleeve 10 and the gall bladder is examined visually by direct viewing. Once the optimal puncture point on the gall bladder has been fixed, two pairs of grasping forceps 30 are introduced through the side instrument channels 13, the inner mouth parts 32 of which forceps are operated by means of scissor handles 31. Tissue portions 42 on the outside of the gall bladder wall 41 are grasped by the forcep mouth parts 32, and the forcep stems 33, which may be Bowden Cables, are clamped by the connectors 14 by turning the bushes 14B in the housings 14A. Alternatively the forcep stems can be fixed by means of a screw or clamp device provided on the housings 14A. For gripping the tissue in the mouth parts 32 of the forceps without further operation of the scissor handles, the handles have fixing means, known per se, such as saw tooth-shaped engaging means. Thus the gall bladder is fixed in position by means of the trocar sleeve 10 with respect to the abdominal wall 40, because the distal end of the trocar sleeve 10 is fixed, thus creating a precondition for reliable introduction of the trocar sleeve insert 20.

Optimal preconditions are thus provided for operation on the gall bladder. A suction cannula with an obliquely cut distal end, designed as a cutting edge, is passed into the surgical optical system or through its instrument channel, into the gall bladder 41, and the gall fluid is extracted through the suction cannula by suction means. If necessary, the gall bladder can be rinsed by means of a rinsing fluid introduced into the gall bladder. For the removal of gallstones, the puncture point in the bladder wall 41 is then extended by means of a scalpel which is introduced, after which the scalpel and the surgical optical system are removed, and the trocar sleeve insert 20 is introduced into the extended bladder wall opening such that its distal end protrudes into the interior of the gall bladder. Provided that the bladder wall incision is not too large, the natural tension of the bladder wall 41 which lies in contact with the outside of the trocar sleeve insert 20 is sufficient to ensure a fluid-tight closure. However sealing can be improved by the use of the sealing lips 23 and 24 which, after introduction of the trocar sleeve insert 20 into the gall bladder, are filled with gas via the valves 26 and the supply lines 25 so that they lie in close contact with the outside or the inside of the gall bladder wall 41.

Preferably the innermost sealing lip 23 is first expanded by the gas supply, and the trocar sleeve insert 20 is then pushed in far enough for the sealing lip 23 to lie in contact with the inside of the gall bladder wall 41, so that the bladder wall 41 can be clamped fluid-tight in this region by inflation of the outer sealing lip 24.

Once the gall bladder has been fixed in position by means of the trocar sleeve 10 and the trocar sleeve insert 20, either the gallstones located in the gall bladder can be sucked out directly through the sleeve 20, or else, if the stones have larger dimensions than the internal diameter of the sleeve 20, they can be broken up before suction removal, by means of known instruments which can be introduced into the gall bladder through the sleeve 20. Once all stones have been sucked out of the gall bladder, the rigid surgical optical system can be exchanged for a flexible endoscope, with which the cystic duct leading to the gall bladder can be examined endoscopically for any particles of stone or other pathological changes. Furthermore, not only the cystic duct but also the pancreas can be checked visually.

Once the stones have been removed from the gall bladder and the investigations concluded, the instruments used, and subsequently the trocar sleeve insert 20, are removed from the body cavity. The opening made in the gall bladder wall for the endoscopic operation is closed again in a known way, for example by clipping, sewing or closing with plaster. Finally, the flexible auxiliary instruments, namely the grasping forceps 32, are detached, and the trocar sleeve 10 can then be removed completely.

A particular advantage of the instrument of the invention, lies in that the organ to be treated can be fixed and held by means of the trocar sleeve 10 and that, by means of the trocar sleeve insert 20, a working channel can be created passing from the outside into the organ, for example the gall bladder, which is sealed off from the abdominal space, which prevents the gall fluid being extracted causing infections in the body cavity.

As well as the stone removal discussed, the instrument according to the invention permits the removal of complete organs by endoscopic means and the obliteration of the gall bladder. In this case, an instrument, known per se, is introduced through the trocar sleeve insert 20 into the body cavity, with which instrument the cystic duct leading to the gall bladder is clipped off, for example. In addition, the cystic duct can, if necessary, be closed by heat supply, which causes a coagulation of the gall bladder tissue and necrosis of the gall bladder mucous membrane. For this purpose, for example, a rinsing fluid at a predetermined temperature is introduced into the gall bladder through the trocar sleever insert. A thermoprobe can be introduced into the gall bladder with the same effect.

Endoscopic treatment methods have the advantage over surgical operations that the patient suffers far less stress and that a stay in hospital which generally lasts several weeks after open surgery is avoided.

What is claimed is:

1. An instrument for endoscopic treatment of internal body organs including the gall bladder comprising a tubular trocar sleeve having an inner diameter, a proximal end and an axial length terminating in a distal end, said trocar sleeve having at least one instrument channel extending axially of the sleeve, said instrument channel having a diameter smaller than the inner diameter of the sleeve, a flexible forceps device having proximal and distal ends separated by a flexible intermediate portion dimensioned to be received through said instrument channel and having a length greater than the instrument channel, said flexible forceps device having a pair of grasping forceps jaws at a distal end thereof and a means for activating the grasping forceps jaws at a proximal end thereof, said sleeve having clamping means carried thereby for fixing the position of the flexible forceps with respect to the instrument channel whereby the flexible forceps are locked in position with respect to the sleeve, said sleeve having an operating length dimensioned to substantially bridge the distance between the abdominal wall and the organ to be treated of a patient after insufflation with the proximal end of the sleeve exterior of the abdominal wall, a trocar sleeve insert having a portion extending from a distal end which has a minimum outer dimension sized to be received axially within the sleeve inner diameter whereby the insert can be pushed into the sleeve proximal end and project out of the distal end of the sleeve, said insert having a working channel therethrough, and said portion having an axial length dimensioned to bridge the distance between the abdominal wall and the organ after insufflation whereby the insert distal end can be inserted into the organ with the distal end of the insert projecting beyond the distal end of the sleeve, said insert portion having an axial length greater than the axial length of the sleeve, said insert having sealing means adjacent its proximal end, said sealing means including a first sealing member adapted to engage against an inside wall of the organ and a second sealing member axially spaced of the first sealing member proximally thereof adapted to sealingly engage and outside of the gall bladder wall.

2. An instrument according to claim 1 wherein the trocar sleeve includes a tubular stem portion and said instrument channel is mounted on the outside of the stem portion.

3. An instrument according to claim 2 wherein two instrument channels are provided mounted on the outside of the stem.

4. The device according to claim 3 wherein the instrument channels terminate in a clamping spigot at proximal ends of the instrument channels and wherein the forceps are adapted to pass through the clamping spigot, said spigots including rotatable bushes and actuator means for rotating the bushes, said bushes effective, upon rotation, to clamp the forceps in position in the instrument channel.

5. An instrument according to claim 4 wherein the trocar sleeve includes a projecting pin adjacent a proximal end of the sleeve for detachably fixing the instrument in position.

6. An instrument according to claim 4 wherein proximal ends of the trocar sleeve and of the trocar sleeve insert are provided with closure means.

7. An instrument according to claim 6 wherein the closure means are elastomer sealing caps having insertion channels therein.

8. An instrument according to claim 6 wherein adjacent to a proximal end of the trocar sleeve insert there is a radially projecting annular shoulder positioned axially along the trocar sleeve insert such that when the trocar sleeve insert is fully pushed into the trocar sleeve, the annular shoulder abuts the sealing means of the trocar sleeve.

9. An instrument according to claim 1 wherein the sealing means are individually inflatable, the insert is provided with inflation channels extending axially therealong from the sealing means to the proximal end of the insert and wherein the sealing means are spaced apart a distance substantially equal to the gall bladder wall thickness.

* * * * *